United States Patent
Itu et al.

(10) Patent No.: US 10,522,253 B2
(45) Date of Patent: Dec. 31, 2019

(54) MACHINE-LEARNT PREDICTION OF UNCERTAINTY OR SENSITIVITY FOR HEMODYNAMIC QUANTIFICATION IN MEDICAL IMAGING

(71) Applicant: Siemens Healthcare GmbH, Erlangen (DE)

(72) Inventors: Lucian Mihai Itu, Brasov (RO); Tiziano Passerini, Plainsboro, NJ (US); Saikiran Rapaka, Pennington, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 192 days.

(21) Appl. No.: 15/796,933

(22) Filed: Oct. 30, 2017

(65) Prior Publication Data

US 2019/0130074 A1 May 2, 2019

(51) Int. Cl.
*G06K 9/00* (2006.01)
*G16H 50/20* (2018.01)
*G06T 7/00* (2017.01)
*G06K 9/62* (2006.01)
*G06K 9/46* (2006.01)
(Continued)

(52) U.S. Cl.
CPC .......... *G16H 50/20* (2018.01); *A61B 6/5217* (2013.01); *G06K 9/4604* (2013.01); *G06K 9/6261* (2013.01); *G06K 9/6265* (2013.01); *G06K 9/6267* (2013.01); *G06N 20/00* (2019.01); *G06T 7/0012* (2013.01); *G06T 7/11* (2017.01); *G06T 7/60* (2013.01); *G16H 30/40* (2018.01); *G16H 50/70* (2018.01); *A61B 6/032* (2013.01); *A61B 6/504* (2013.01); *A61B 6/507* (2013.01); *G06T 2200/24* (2013.01); *G06T 2207/10081* (2013.01); *G06T 2207/20076* (2013.01); *G06T 2207/20081* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS 6,408,201 B1 * 6/2002 Foo .................. A61B 5/055
324/300
9,349,178 B1 5/2016 Itu et al.
(Continued)

OTHER PUBLICATIONS

Extended European Search Report (EESR) dated Feb. 19, 2019 in corresponding European Patent Application No. 18202735.9.
(Continued)

*Primary Examiner* — Shervin K Nakhjavan

(57) ABSTRACT

The uncertainty, sensitivity, and/or standard deviation for a patient-specific hemodynamic quantification is determined. The contribution of different information, such as the fit of the geometry at different locations, to the uncertainty or sensitivity is determined. Alternatively or additionally, the amount of contribution of information at one location (e.g., geometric fit at the one location) to uncertainty or sensitivity at other locations is determined. Rather than relying on time consuming statistical analysis for each patient, a machine-learnt classifier is trained to determine the uncertainty, sensitivity, and/or standard deviation for the patient.

20 Claims, 10 Drawing Sheets

(51) Int. Cl.
   *G06T 7/11*    (2017.01)
   *G06T 7/60*    (2017.01)
   *A61B 6/00*    (2006.01)
   *G06N 20/00*   (2019.01)
   *G16H 30/40*   (2018.01)
   *G16H 50/70*   (2018.01)
   *A61B 6/03*    (2006.01)

(56) References Cited

U.S. PATENT DOCUMENTS

| | | | | |
|---|---|---|---|---|
| 10,169,543 | B2* | 1/2019 | Taylor | A61B 5/026 |
| 2014/0249784 | A1* | 9/2014 | Sankaran | A61B 6/504 |
| | | | | 703/2 |
| 2015/0359601 | A1* | 12/2015 | Sauer | G06T 7/0012 |
| | | | | 382/128 |
| 2016/0148371 | A1* | 5/2016 | Itu | G16H 50/50 |
| | | | | 382/128 |
| 2016/0166209 | A1* | 6/2016 | Itu | A61B 5/026 |
| | | | | 600/408 |
| 2016/0310018 | A1* | 10/2016 | Fonte | A61B 6/504 |
| 2017/0039340 | A1 | 2/2017 | Sankaran et al. | |

OTHER PUBLICATIONS

Taylor, Charles A., Timothy A. Fonte, and James K. Min. "Computational fluid dynamics applied to cardiac computed tomography for noninvasive quantification of fractional flow reserve." Journal of the American College of Cardiology 61.22 (2013): 2233-2241.

Sankaran, Sethuraman, Leo Grady, and Charles A. Taylor. "Impact of geometric uncertainty on hemodynamic simulations using machine learning." Computer Methods in Applied Mechanics and Engineering 297 (2015): 167-190.

Coenen, Adriaan, et al. "Fractional flow reserve computed from noninvasive CT angiography data: diagnostic performance of an on-site clinician-operated computational fluid dynamics algorithm." Radiology 274.3 (2014): 674-683.

Haggerty, Christopher M., et al. "Simulating hemodynamics of the Fontan Y-graft based on patient-specific in vivo connections." The Journal of thoracic and cardiovascular surgery 145.3 (2013): 663-670.

Itu, Lucian, et al. "A machine-learning approach for computation of fractional flow reserve from coronary computed tomography." Journal of Applied Physiology 121.1 (2016): 42-52.

Renker, Matthias, et al. "Comparison of diagnostic value of a novel noninvasive coronary computed tomography angiography method versus standard coronary angiography for assessing fractional flow reserve." The American journal of cardiology 114.9 (2014): 1303-1308.

Sankaran, Sethuraman, Leo Grady, and Charles A. Taylor. "Fast computation of hemodynamic sensitivity to lumen segmentation uncertainty." IEEE transactions on medical imaging 34.12 (2015): 2562-2571.

* cited by examiner

MACHINE-LEARNT PREDICTION OF UNCERTAINTY OR SENSITIVITY FOR HEMODYNAMIC QUANTIFICATION IN MEDICAL IMAGING

BACKGROUND

The present embodiments relate to hemodynamic quantification in medical imaging. Blood-flow computations provide important insights into the structure and function of the cardiovascular system. For coronary artery disease (CAD), the functional index of fractional flow reserve (FFR) has been predicted from medical imaging by employing computational fluid dynamics (CFD). These CFD-based models combine geometrical information extracted from medical imaging with background knowledge on the physiology of the system, encoded in a complex mathematical fluid flow model consisting of partial differential equations. This approach leads to a large number of algebraic equations, making it computationally very demanding, preventing adoption of this technology for real-time applications such as intra-operative guidance of interventions. An alternative and less computationally expensive approach is based on machine learning (ML) algorithms. The relationship between input data and quantities of interest (e.g., FFR) is represented by a model built from a database of samples with known characteristics and outcome.

The accuracy of the predictions depends on the quality and accuracy or precision of the input information, as well as on the assumptions of the models. The main source of uncertainty for quantities of interest extracted from patient-specific blood flow computations may be represented by the anatomical model reconstructed from medical images. The resolution and precision of the acquisition scans, the segmentation, the reconstruction, and specific patient conditions (e.g., age, gender, or BMI) represent the some causes for the uncertainties. The predicted quantity has an unknown level of accuracy, making it more difficult for the physician to use the quantification.

Previous approaches directed at estimating the geometric sensitivity typically focused on the influence of the geometric uncertainty on the FFR values in the same region. This information may assist in deciding whether to use a quantification, but does not provide information that may be used to improve the quantification for that patient.

SUMMARY

By way of introduction, the preferred embodiments described below include methods, systems, instructions, and non-transitory computer readable media for hemodynamic quantification. The uncertainty, sensitivity, and/or standard deviation for a patient-specific hemodynamic quantification is determined. The contribution of different information, such as the fit of the geometry at different locations, to the uncertainty or sensitivity is determined. Alternatively or additionally, the amount of contribution of information at one location (e.g., geometric fit at the one location) to uncertainty or sensitivity at other locations is determined. Rather than relying on time consuming statistical analysis for each patient, a machine-learnt classifier is trained to determine the uncertainty, sensitivity, and/or standard deviation for the patient.

In a first aspect, a method is provided for hemodynamic quantification in a medical imaging system. The medical imaging system scans the patient. The scanning provides cardiac data representing part of a cardiac system of the patient. A patient-specific cardiac geometry is determined from the cardiac data. Values for features of a first input vector of a machine-learnt predictor of the hemodynamic quantification are extracted from the patient-specific cardiac geometry. The machine-learnt predictor predicts a value of the hemodynamic quantification in response to the values of the features of the first input vector. Values for features of a second input vector of a machine-learnt classifier of uncertainty and/or sensitivity of the hemodynamic quantification are extracted. The machine-learnt classifier classifies a value or values of the uncertainty and/or sensitivity of the hemodynamic quantification to the patient-specific cardiac geometry in response to the values for the features of the second input vector. An output is generated based on the value of the hemodynamic quantification and the value or values of the uncertainty and/or sensitivity.

In a second aspect, a system is provided for hemodynamic quantification. A medical scanner for scanning a patient is configured to output coronary data for the patient. An image processor is configured to extract a patient-specific coronary geometry from the coronary data, compute a hemodynamic quantity for a first location on the patient-specific coronary geometry, determine a confidence statistic of the hemodynamic quantity associated with a second location different than the first location. A display is configured to display the hemodynamic quantity and the confidence statistic.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Uncertainty and/or sensitivity in hemodynamic computation is predicted. A machine-learnt classifier is used for real-time or prediction with less computational requirements than statistical analysis. Computing uncertainty and/or sensitivity is integrated efficiently in clinical workflows and in the decision-making process. Given the intrinsic uncertainty of the quantities of interest, decision making based on the computed metrics of interest (e.g. FFR) remains subjective. Hence, there is a need to enable a fully automated or semi-automated assessment of the uncertainty for the computed metric of interest (e.g. FFR). The assessment is provided alongside the nominal value of the metric. By having access to both the nominal value and a measure of the uncertainty, the clinical operator will be able to make a more informed decision. Additionally, the uncertainty analysis indicates the locations in the coronary tree that have the largest influence on the computed quantity of interest. Based on the spatial distribution of influence, the user may focus more on these regions when preparing the input data for computing the quantity of interest to increase the confidence in the output value (i.e., to reduce the uncertainty).

In a workflow, the sensitivity and/or uncertainty of hemodynamic quantities computed through machine-learnt predictors or other approaches are determined. The sensitivity and/or uncertainty are determined with respect to the uncertainty of the anatomical model reconstructed from the medical images or with respect to other information used to quantify. In one embodiment, medical imaging data of the coronary arteries of a patient is acquired. Features are extracted from the medical imaging data representative of the coronary anatomical model. A machine-learnt predictor or CFD model predicts a quantity of interest for each lesion in the coronary arterial tree. The sensitivity and/or uncertainty of the quantity of interest is computed with respect to the anatomical model. The quantity of interest is visualized alongside its sensitivity and/or sensitivity.

In the examples used herein, the hemodynamic quantity and sensitivity and/or uncertainty are calculated for coronary circulation. In other examples, the quantity and sensitivity and/or uncertainty are calculated for other parts of the cardiovascular system, such as within the heart or vessels at other locations.

Various techniques may be employed to perform the sensitivity and/or uncertainty analysis. For example, any of reliability methods, stochastic expansion methods (e.g., polynomial chaos expansion, or stochastic collocation), importance sampling, adaptive sampling, interval analysis, Dempster-Shafer theory of evidence, or Bayesian calibration are used. The analysis is performed for a given patient. Alternatively, the analysis is performed to train a machine-learnt classifier to output the sensitivity and/or uncertainty for a specific patient.

Figure 1:
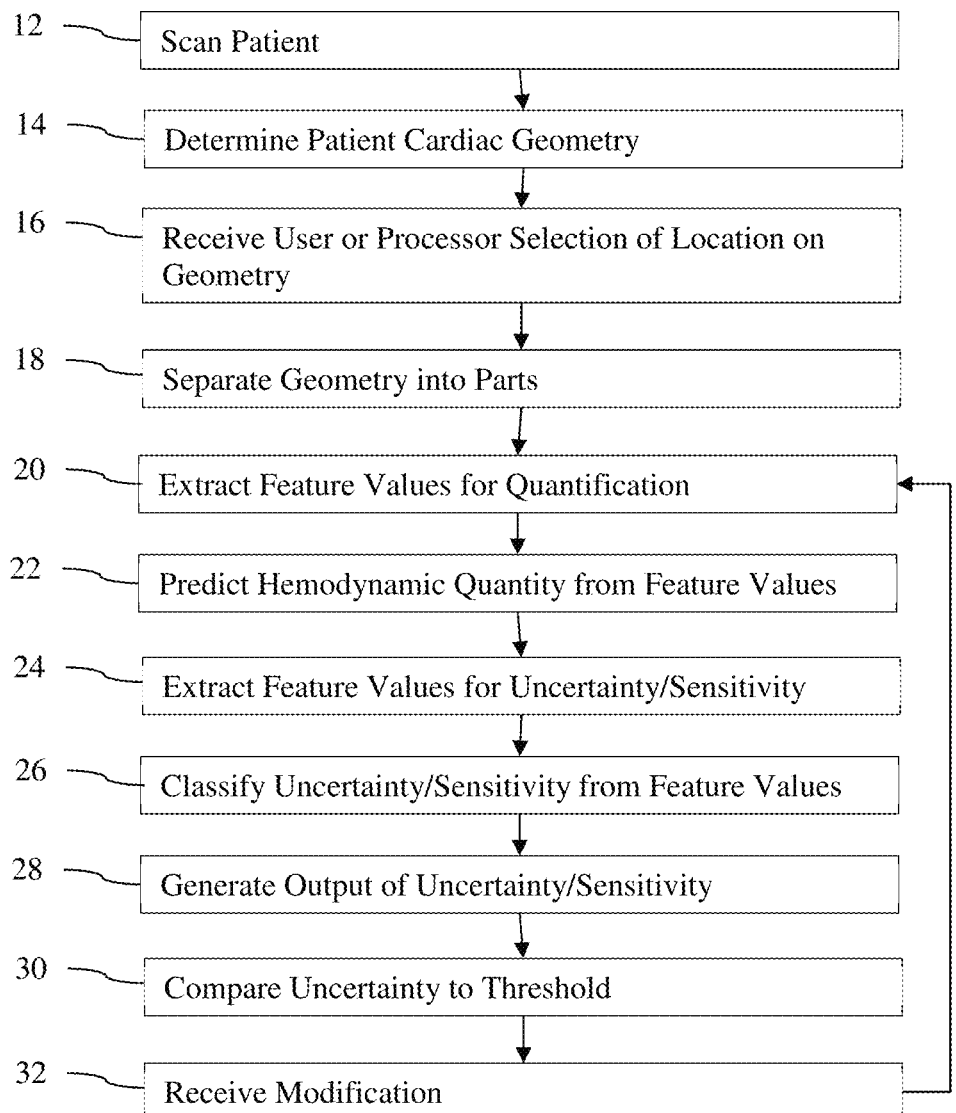
FIG. 1 is a flow chart diagram of one embodiment of a method for hemodynamic quantification in a medical imaging system.

FIG. 1 is a flow chart of one embodiment of a method for hemodynamic quantification in a medical imaging system. The sensitivity and/or uncertainty are determined for one or more hemodynamic predictions. The relationship of the uncertainty as a function of location to the prediction, and/or the relationship of uncertainty of one location to predictions at other locations is provided. The classification of the uncertainty and/or sensitivity may be performed by a machine-learnt classifier.

Figure 2:
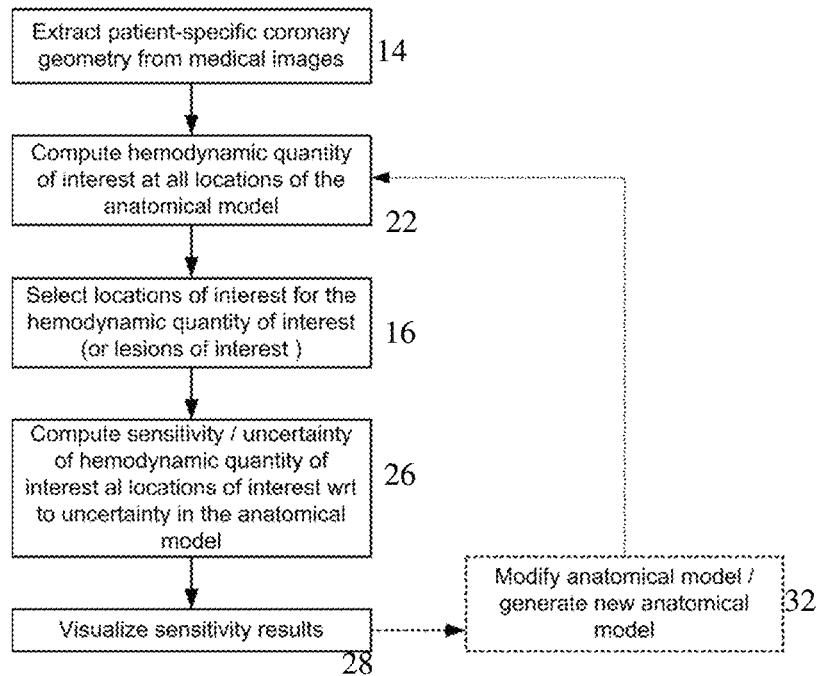
FIG. 2 is a flow chart diagram of another embodiment of a method for hemodynamic quantification in a medical imaging system.

FIG. 2 shows another embodiment of the method. This embodiment represents a workflow for evaluation of geometric sensitivity of hemodynamic quantification.

The acts are performed in the order shown (e.g., top to bottom or numerical) or other orders. For example, FIG. 1 shows act 22 performed after act 16, and FIG. 2 shows act 22 performed before act 16. The acts 20 and 22 may be performed before or simultaneously with acts 24 and 26.

Additional, different, or fewer acts may be provided. For example, FIG. 2 shows using a subset of the acts of FIG. 1. As another example, acts 20 and 24 are combined into one act. In yet another example, any of acts 14, 18, 28, 30, and/or 32 may not be provided. In another example, act 20 is not provided where act 22 is performed with CFD, and/or act 24 is not performed where act 26 is computed as a numerical or computational solution. Acts for configuring a medical scanner may be provided.

Figure 20:
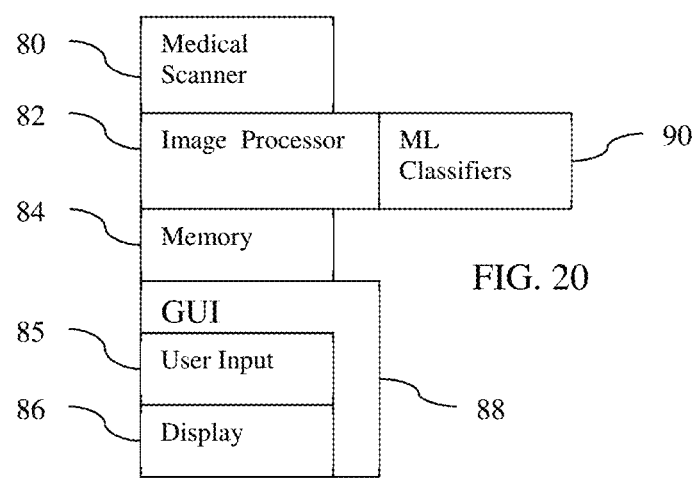
FIG. 20 is one embodiment of a system for hemodynamic quantification with provision for uncertainty, sensitivity, and/or standard deviation of the quantification.

The acts are performed by the system of FIG. 20 or another system. For example, act 12 is performed by a CT scanner, acts 16 and/or 32 are performed by a user input device or processor, and the other acts are performed by a processor. In one example, the medical scanner performs all the acts. In yet another example, a workstation, computer, portable or handheld device (e.g., tablet or smart phone), server, or combinations thereof perform one or more of the acts. In one embodiment, a workstation determines the sensitivity during the medical examination of a patient (i.e., within a few minutes of completion of a scan of the patient, during an appointment for the scan, and/or in real-time with the scan).

In act 12, one or more medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format (i.e., scan or voxel data). As another example, the medical image may be a plurality red, green, blue (e.g., RGB) values output to a display for generating the image in the display format. The medical image may not yet be a displayed image, may be a currently displayed image, or may be previously displayed image in the display or other format. The image is a dataset that may be used for anatomical imaging, such as scan data representing spatial distribution of anatomy (e.g., coronary arteries) of the patient.

The medical image is obtained by loading from memory and/or transfer via a computer network. For example, previously acquired scan data is accessed from a memory or database. As another example, scan data is transmitted over a network after acquisition from scanning a patient. In other embodiments, the medical image or scan data is obtained by scanning the patient with a medical imaging system.

Any type of medical image may be used. In one embodiment, a CT scanner or system acquires CT scan data representing a patient. CT scan data is acquired by rotating a source of x-rays and an opposing detector about a patient. Any range and/or path of travel may be used, such as rotating along a helical path of travel. C-arm or other x-ray imaging may be used instead, such as an x-ray angiography system. Computed tomography is then used to determine the two or three-dimensional distribution of x-ray attenuation from the projections detected by the detector. In other embodiments, other types of scan data or medical images are obtained, such as magnetic resonance, x-ray, ultrasound, positron emission tomography (PET), or single photon emission computed tomography (SPECT).

In one embodiment, coronary CT angiography is performed to acquire the coronary CT data representing a heart or coronary region of the patient. Other coronary CT data may be acquired, such as Dual Energy or Photon Counting data. The coronary CT data is acquired for a stable or acute patient being examined for coronary artery disease. Other cardiac data representing the coronary and/or other parts of the cardiac system may be provided.

Based on the received detected intensities, a three-dimensional representation of the patient (i.e., the density or absorption as a function of voxel or location) is generated by computed tomography processing. Alternatively, the scan data represents a two-dimensional cross-section of the patient. Data representing an interior region of a patient is obtained. The frame of data represents a two or three-dimensional region of the patient. Values are provided for each of multiple locations distributed in two or three dimensions.

Besides the coronary data, input information for quantification and/or sensitivity analysis may be extracted from one or more other sources. Other medical equipment and devices, such as a stethoscope, blood pressure meter, and/or laboratory diagnostics (e.g., blood pressure, heart rate, ECG signals), may be used to provide patient data. Other example data include any one or more of: the type of patient (e.g., stable or acute), results of previously performed non-invasive stress tests (e.g., Myocardial Perfusion Imaging (MPI), Multigated Acquisition (MUGA) Scan, Radionuclide Stress Test and Nuclear Stress Test, Exercise Stress Test, Electrocardiogram (EKG/ECG), and/or Stress or rest echocardiography), measurements from non-medical grade devices (e.g. wearables, watches, pedometers, smartphones, and/or tablets), biochemical signals as produced by blood tests and/or molecular measurements (e.g., proteomics, transcriptomics, genomics, metabolomics, lipidomics, and epigenomics), features extracted based on radiogenomics (imaging biomarkers that are linked with the genomics of a pathology), demographic information (e.g., age, ethnicity, gender, weight, height, race, body max index (BMI), diabetes, hypertension, hypercholesterolemia, smoking history, family history of CAD, prior myocardial infarction (MI), prior PCI, prior CABG, and/or angina type (e.g., stable/worsening/silent ischemia/other angina category, according to CCS, AHA/ACC)), clinical history of the patient (e.g., the patient may have been exposed to radiation recently due to other medical exams), and/or genetic, radiogenomic or other phenotype based features of the patient.

Any sub-set or all these different types of information may be acquired at a single time point or at different time points. For example, features extracted from a previous coronary angiography or from an angiographic exam may be used to predict one or more measures of interest. Similarly, blood biomarkers (the same or different) may be acquired at different time points and used as features. The same type of information may be acquired at different times, providing a time series of information. One type of information may be acquired at a same or different time as another type of information.

In act 14, an image processor determines a patient-specific cardiac geometry from the cardiac data. The geometry is determined as a mesh or surface. The cardiac geometry is segmented from the cardiac data. Gradients, thresholds, random walker, or other image process determines the geometry. Alternatively, a generic model or other geometric representation is fit to the cardiac data. Landmarks may be detected and used for fitting. Correlation may be used for fitting. Any now known or later developed image process to find heart, vessel, or another cardiac surface may be used.

The geometry is specific to the patient. Rather than using a generic representation, the geometry for this patient is found. The geometry may indicate a lesion, such as a stenosis or other flow-affecting structure. The geometry is of any extent, such as representing a single vessel for any length or representing a vessel tree of any number of branches.

In act 16, one or more locations of interest are identified. The image processor receives the location or locations. The location or locations are parts of the patient-specific geometry. For example, any location corresponding to a stenosis is identified. In another example, one or more locations for each segment (i.e., portion between branches) are identified, such as a terminal location for each segment.

Figure 3:
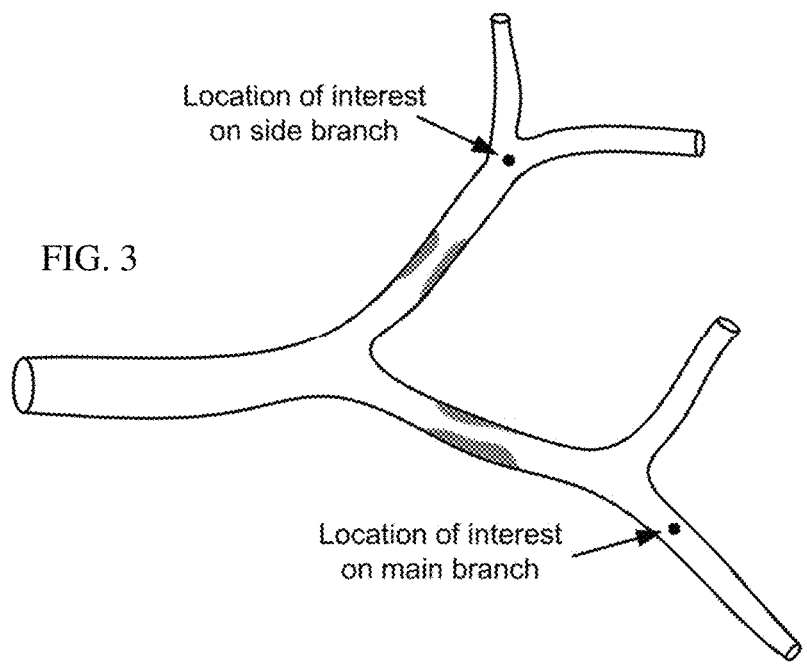
FIG. 3 illustrates an example coronary vessel tree with multiple stenoses and corresponding locations of interest.

The locations are identified manually or automatically. For manual, the user selects the locations on a rendering of the geometry and/or rendering of the cardiac data. Using the user interface (e.g., display and user input device), the user selects any number of locations for which the user desires to have a prediction of the hemodynamic quantification (e.g., FFR). The locations may correspond to lesions of interest, downstream locations to lesions, or other positions. For example, the user selects a lesion to determine the influence of the lesion on the computed quantity of interest. FIG. 3 shows a vessel tree geometry with two user selected locations of interest, one past a lesion on a main branch and the other past a lesion on a side branch. The user may select the location at which invasive measurement would have been performed. The sensitivity values are to be computed with respect to the selected location.

The location or locations may be identified by an image processor. For example, locations of turbulent flow, restriction, or another landmark are found. Template fitting, centerline analysis, flow analysis, segmentation, or other process may be used. In one embodiment, a machine-learnt detector detects the location or locations. Automatically chosen locations may be modified or discarded by the operator. Alternatively, the operator may add other locations of interest.

In one embodiment, the sensitivity is to be determined for different locations with respect to the computed quantity (e.g., FFR value) at a certain location. A fully automated sensitivity analysis is provided. The user does not indicate a location on the geometry or on a rendering from the cardiac data.

In act 18, any separation of the patient-specific cardiac geometry may be used. By separating the geometry into vessel branches, separate prediction of the hemodynamic quantity for each branch and corresponding sensitivity with respect to the location are provided branch by branch. The sensitivity at the location of the quantification, the sensitivity of the quantification at the location to uncertainty at other locations, and/or the sensitivity of quantifications at other locations to uncertainty at one location are separately classified for each branch. In alternative embodiments, the sensitivity of a quantification with respect to uncertainty over the branch and other branches is used.

Figure 4:
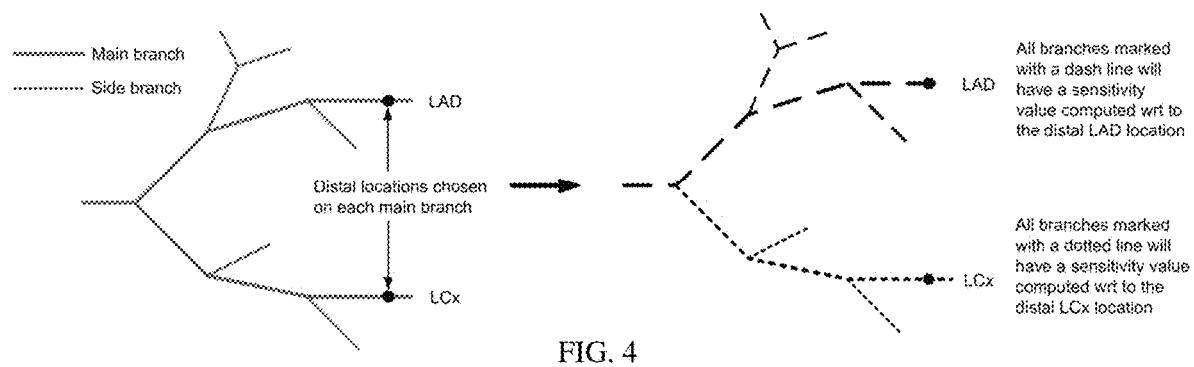
FIG. 4 illustrates an example coronary vessel tree with locations of interest based on main or non-terminal branches.

FIG. 4 shows an example approach. A distal location is chosen on each main branch (e.g., LAD, LCx, and/or RCA)

included in the vessel tree. In FIG. 4, the LAD and LCx main branches are included in the geometry. Since the hemodynamics in the three main branches have little influence on each other, a sensitivity map is computed separately for each main branch and its corresponding side branches. In FIG. 4, the LAD main branch and side branches are shown as dashed lines with the quantification being for a terminal end of the LAD main branch, and the LCx main branch and side branches are shown as dotted lines with the quantification being for a terminal end of the LCx main branch. The image processor identifies the main branches and selects the locations at or near terminal ends of the main branches.

The flow in the main branches may influence each other if collateral flow exists. A location in each main branch near the bifurcation of the main branches may be selected.

Figure 5:
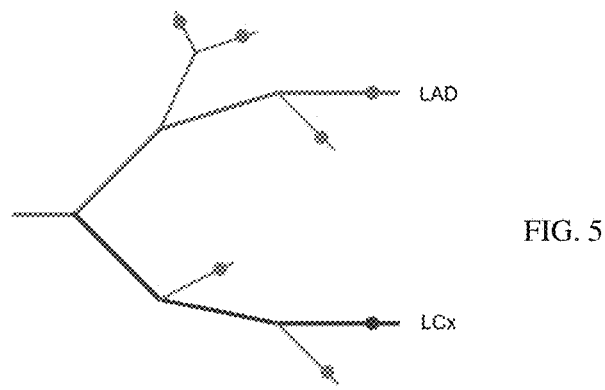
FIG. 5 illustrates the example coronary vessel tree of FIG. 4 with locations of interest based on terminal and non-terminal branches.

Using the approach of FIG. 4, side branches may typically have little influence on the quantification value at a distal location of the main branch. To determine quantification values and corresponding sensitivity for the side branches, a different approach may be used. FIG. 5 shows an example using the geometry from FIG. 4. For predicting the hemodynamic quantification value, a distal location is chosen on each terminal branch, whether a main or side branch. The sensitivity values on each terminal branch are computed in relation to the distal location chosen on that branch. For all non-terminal branches (i.e., main branches), the sensitivity values are computed in relation to the distal location chosen on the largest terminal branch. The sensitivities are computed for locations along the entire main branch without the side branches.

In act 20, the image processor extracts values for features of an input vector of a machine-learnt predictor of the hemodynamic quantification from the patient-specific cardiac geometry. Values for features from other sources, such as the cardiac data, patient information, other measurements, or clinical data, may alternatively or additionally be extracted. A sub-set of the acquired data from act 12, act 14 and/or other sources is selected. Alternatively, acts 12 and 14 are only performed for the features of the input vector, so acquisition may be extraction. The machine-learnt or other predictor uses a given set of features. Patient data available for those features is used to determine the value of the features.

The extraction may be selecting or determining the value. For example, centerline location, radius, and/or circumference shape of the vessel geometry is extracted for a plurality of locations along the vessel tree, such as for multiple locations along each segment or branch. The FFR may be more sensitive to radius, so radii along a vessel represented by the patient-specific cardiac geometry are extracted. The sensitivity with respect to the anatomical model reconstructed from the medical images of the patient may be the focus for quantification. Alternatively, any features used by the machine-learnt predictor for predicting the measure of interest may be extracted directly from the medical images of the patient without generating an anatomical model of the vessels. For example, filter kernels (e.g., Haar wavelets or neural network learnt kernels) are applied to the cardiac data and the results are the values of the features. In this case, the uncertainty related to the anatomical information may be incorporated directly into these features. As another example, anatomical, functional, measured, or other values of acquired patient data are used as values for the input vector. Alternatively, the extraction alters the acquired values, such as by filtering or combining information.

Different predictors may use different input vectors. Different sets of values may be extracted for different predictors. Alternatively, one set is extracted for all predictors or only one predictor. Similarly, the same or different features are used for predicting the quantification and classifying the sensitivity (i.e., same or different features for acts 20 and 24).

Where the quantification is performed without a machine-learnt predictor, then values of features may not be extracted. Alternatively, the extracted values are for variables used in the quantification, such as values related to the patient-specific geometry for CFD.

In act 22, a machine-learnt predictor, applied by the image processor, predicts a value of the hemodynamic quantification for the patient. The extracted values are input to the machine-learnt predictor. The input is by applying the values to the matrices representing the machine-learnt predictor. In response to the values of the features of the input vector, the machine-learnt predictor outputs a value for the quantification. The quantity of interest is computed.

Any one or combinations of hemodynamic quantities may be predicted. In one embodiment, FFR is computed. Other hemodynamic quantities include instantaneous wave-free ratio (iFR), rest Pd/Pa, CFR, HSR, BSR, IMR, and/or wall shear stress.

The machine-learnt predictor predicts the value of the hemodynamic quantification for one or predicts values for more locations. For example, the FFR is predicted at one location (e.g., at a lesion) or at multiple locations. For FIG. 3, the FFR is predicted at two locations. For FIG. 4, the FFR is predicted at two locations (dots). For FIG. 5, the FFR is predicted at seven locations. In other embodiments, the FFR is predicted at multiple locations in each branch and/or segment of the patient-specific geometry. FFR may be computed for all or multiple locations in a mesh fit to the coronary arterial tree (i.e., the patient specific geometry). The features used to predict at any given location are based on information representing that location. Features from other locations may be used as well for predicting at a given location. Features that are not location specific may be used.

The machine-learnt predictor is trained to make the prediction based on training data. The training data includes samples of the input feature vector from many instances with known quantification results (ground truth). For example, extracted values from many patients are provided where CFD and/or invasive measurement are used to establish the ground truth. The machine training learns to predict the result based on the values of the input feature vector.

A desired number and/or diversity of patient samples may not be available for training or there may be a prohibitive cost in acquiring. To overcome this, the machine-learnt predictor may be trained entirely or at least partially on synthetic examples. A large synthetically generated database of coronary anatomies is created, resulting in a rich sampling of the different morphologies of coronary blockage. For example, the machine learning model is trained to learn the relationship between anatomical features and the FFR values computed using the CFD model where some or all the examples of anatomy are synthetically created. Rather than using data for an actual patient, data is generated by perturbing patient data to create samples not from an actual patient. A non-patient physical model (e.g., tubes to represent the coronary artery tree with fluid simulating blood and a pump simulating pressure from the heart) may be used. Generic or non-patient specific computer modeling may be used to generate the data. Synthetic images, synthetic anatomical models, and/or other non-patient-specific data may be used.

Any machine learning or training may be used. A probabilistic boosting tree, support vector machine, neural network (e.g., deep learning), sparse auto-encoding classifier, Bayesian network, or other now known or later developed machine learning may be used. Any semi-supervised, supervised, or unsupervised learning may be used. Hierarchal or other approaches may be used. In one embodiment, the classification is by a machine-learnt classifier learnt with deep learning. As part of identifying features that distinguish between different outcomes, the classifier is also machine learnt. Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. Hierarchical structures are employed, either for learning features or representation or for classification or regression. The computer-based decision support system employs a machine learning algorithm for automated decision making.

In alternative embodiments, a model other than a machine-learnt predictor is used. Rule based (e.g., decision tree), reduced order (e.g., lumped parameter model of the coronary circulation system), or other models are used. For example, CFD is performed using the patient-specific geometry. The model of the geometry fit to the patient data may include biomechanical, physics, and/or other elements for modeling blood flow through the geometry.

Acts 24 and 26 are directed to classifying statistical information about the confidence of the quantification, such as the uncertainty and/or sensitivity. In the example of FIG. 1, the classification uses a machine-learnt classifier. In the example of FIG. 2, the classification uses a machine-learnt classifier or another approach, such as numerical computation of the sensitivity. Below, the machine learning for classifying is discussed. As part of the training, the ground truth sensitivity and/or uncertainty are determined. The numerical computation approach performs the calculations used to create the ground truth, but for the specific patient rather than for various training samples.

Figure 6:
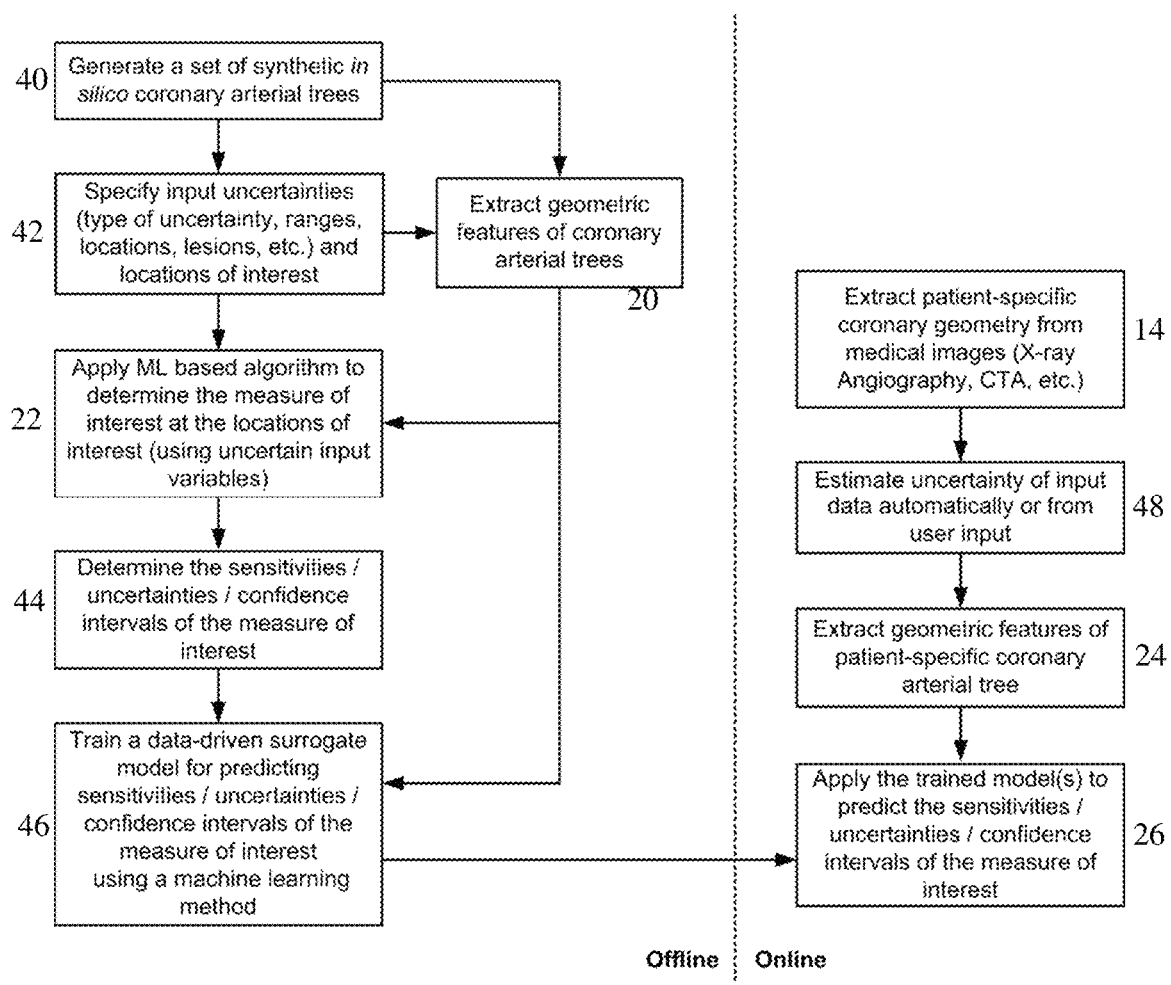
FIG. 6 is a flow chart diagram showing one embodiment of training and applying a machine-learnt classifier of uncertainty or sensitivity.

FIG. 6 shows an offline set of acts for training and an online set of acts for applying the machine-learnt classifier. Acts 40, 20, and 22 correspond to training (act 40) and application of the machine-learnt predictor of the hemodynamic quantification. The machine-learnt predictor is trained based, at least in part, on a generated set of synthetic arterial trees in act 40. In act 20, values for geometric features, with or without other features, are extracted. In act 22, the machine-learnt predictor is used as a forward model in assessing the sensitivity and/or uncertainty. Since the forward model employed in the assessment of the sensitivity and/or uncertainty is based on a machine-learnt predictor, each forward run (i.e., quantification based on one sample of the training data) requires only a short execution time. Since, typically, a very large number (e.g., hundreds, thousands, or more) of samples are generated due to the large number of uncertain variables, the sensitivity computation may still require a considerable amount of time. To mitigate this limitation for classifying the confidence statistic for a given patient, the machine-learnt classifier or classifiers may be trained and applied to directly determine the sensitivity, uncertainty, and/or confidence intervals associated with a measure of interest, locations, and/or lesions of interest in act 46.

In act 42, the input uncertainties (type of uncertainty, ranges, locations, lesions, etc.) are specified for the locations of interest. In act 20, the set of extracted features includes not just the characteristics of the coronary anatomical model but also uncertainty related aspects. In the training of act 46, the values of these features are used. The features for uncertainty may or may not be used by the forward model. In act 22, forward model (i.e., machine-learnt predictor for quantification) is employed to propagate this uncertainty, and, as a result, the sensitivity, uncertainty, and/or confidence intervals associated with the measure of interest are determined in act 44. The classification of the sensitivity, uncertainty, and/or another confidence statistic may then be learned in act 46 through a machine learning algorithm based on the extracted features.

In application to a particular patient (i.e., online), the patient-specific geometry is determined in act 14. The uncertainty information in the input data is specified in act 48 either automatically or by the user. For example, the given imaging configuration and patient data are used to determine the uncertainty in the geometry and/or other input feature information based on known uncertainty in the system (e.g., x-ray intensity variation) and/or assumed or estimated uncertainty (e.g., BMI effects) for the given type and configuration of scanning. The same features used for training are extracted in act 24 for a patient-specific geometry. In act 26, the machine-learnt classifier outputs the sensitivity, uncertainty, and/or confidence intervals associated with the measure of interest.

The machine-learnt classifier employed for predicting sensitivity, uncertainty, and/or confidence intervals may be run in parallel with the machine-learnt predictor or forward model used to compute the nominal value of the quantity of interest. Where neural networks are employed as machine learning algorithms for both the predictor and classifier, the neural networks used to predict the measure of interest and sensitivity, uncertainty, and/or confidence intervals associated with the measure of interest may share one or more layers. The prediction of the various quantities may be performed simultaneously with the classification of the sensitivity and/or uncertainty whether layers are shared or not.

One advantage of a machine-learnt classifier is that the online prediction for a given patient is fast: results are output almost instantaneously (e.g., in a matter of seconds). The machine-learnt predictor and classifier may be run directly on the workstation located at clinics or hospitals and during an appointment of the patient or as needed by a physician. In alternative embodiments, a remote server is used. A combination of local and remote may be used. Off-site or remote processing may enable a more accurate sensitivity analysis, which is enabled by the less strict requirement on the processing time. Examples of such scenarios include employing a complex computational model (CFD) available off-site but not on-site. On-site assessment may not be available at the time when the medical images are acquired. This may be due to limitations of the imaging workstation (e.g., incompatible hardware or software configuration) or unavailability of the workstation providing the processing functionality. In this case, off-site processing may be offered as an alternative to produce the same results as the on-site counterpart or with the possibility of choosing different analyses or options. In another scenario, the on-site assessment provides a first approximation of the sensitivity and/or uncertainty analysis (e.g., not all image features are extracted with confidence). In this case, off-site processing includes further image processing to extract more image features or with more confidence (i.e., less uncertainty). Off-site processing may also include evaluating a larger set of features (e.g. non-image features such as clinical history of the patient, risk factors for fractures, etc.) incorporated in the predictor and/or classifier to improve the assessment.

In act 24 of FIG. 1, the image processor extracts values for features of the input vector of the machine-learnt classifier of uncertainty and/or sensitivity of the hemodynamic quantification. For example, the radii of different locations of the patient-specific anatomy are extracted. Other geometric information may be extracted, such as the centerline, circumference shape, and/or the branch information. The uncertainty in the anatomical information on the measure of interest is to be classified. In other embodiments, other sources of uncertainty of the quantification may be used, such as demographic characteristics (age, gender, weight, height, BMI, etc.), patient characteristics determined during or before the medical imaging exam (blood analysis, biomarkers, heart rate, blood pressures, etc.), and/or information from previous medical exams (imaging/non-imaging) of the patient (e.g., change in size of a lesion).

The same or different features are used for classifying the sensitivity and/or uncertainty as used for predicting the quantity. In one embodiment, features about the source of uncertainty are extracted. For example, the type of scan, the scan settings, reconstruction, patient characteristics, or other system or process-related sources may have assumed or known uncertainties. Given the patient and patient scan information, features may be extracted from or of these sources of uncertainty.

In act 26, the machine-learnt classifier, based on application by the image processor, classifies a value or values of the confidence statistic, such as the uncertainty and/or sensitivity, of the hemodynamic quantification to the patient-specific cardiac geometry. The classification may be of the uncertainty and/or sensitivity of the quantification to other sources of uncertainty. The classification is in response to the values for the features of the input vector. The classification is provided with no user interaction, but user interaction may be provided. The values for the features are applied to the classifier. The matrix or matrices representing the classifier output the sensitivity and/or uncertainty based on the input values.

The sensitivity and/or uncertainty are computed based on the locations and/or lesions of interest and the results are visualized. The classification may be for a same location as the prediction of the value of the quantity. The classification occurs for all the locations of interest for which FFR or other quantification is performed.

In further embodiments, the classification of the sensitivity and/or uncertainty is for other locations than the location at which the quantification is performed. The sensitivity and/or uncertainty for other locations with respect to the quantification for a different location is classified. In a first embodiment, the sensitivity of a quantification for one location with respect to the uncertainties at other locations is found. In a second embodiment, the sensitivity of quantifications for other locations with respect to the uncertainty for a given location is found. The spatial distribution provides information allowing the physician or other to focus efforts for improving the confidence of the quantification. Where to verify or alter the geometry to better fit the cardiac data of the patient is found. Alternatively or additionally, which variables (e.g., radii vs. BMI vs. reconstruction setting) to correct or verify are found.

For the first embodiment, the sensitivity for a set of locations of interest is computed. The sensitivity and/or uncertainty of the quantity of interest at one or more specific locations of interest is computed. For example, FFR is typically determined at a location downstream from the main stenosis. This means that in a workflow where FFR is determined, a clinician may be interested in the sensitivity and/or uncertainty of the computed FFR value at that distal location with respect to different sources of uncertainty elsewhere in the branch including or not including the location of the FFR.

Once the locations of interest have been defined, the image processor determines a separate sensitivity map (i.e. sensitivity at each location of the anatomical model) for each location of interest. The classifier provides the map as output. The classifier is trained using the sensitivity analysis discussed below or the classifier implements the sensitivity analysis for a particular patient.

In one embodiment, the sensitivity and/or uncertainty analysis operates as follows. This example provides for sensitivity of FFR computed using the machine-learnt predictor. Uncertainty, standard deviation, or confidence intervals may be classified. The sensitivity or other parameter for other quantifications may be provided.

The uncertain input variables for instance the radius of the vessel, is determined. Any geometric or non-geometric input variable may be used. The input variable has a level of uncertainty due to various factors. The factors include the scan type (e.g., CCTA, X-ray Angiography, etc.), scan settings (e.g., tube voltage, tube current, exposure time, table speed, scanner properties), reconstruction algorithm and settings, patient characteristics (age, gender, BMI, patient state, etc.), or others. Using known, assumed, or estimated uncertainties for the contributing factors, an uncertainty for the input variable may be determined.

Rather than processing for each sample location along the geometry, a subset of all locations (cross-sections) is selected based on a given spacing (e.g. 0.5 mm). One uncertain variable is associated with each selected location. Alternatively, a separate uncertain variable may be associated with an entire vessel region. For example, for healthy vessel regions, a single uncertain variable may be defined, while for the stenotic regions multiple uncertain variables may be defined. Alternatively, separate uncertain variables may be defined for different branches (LAD, LCx, RCA, side branches, etc.).

The uncertainty is used to determine a distribution to be used to estimate sensitivity. The machine-learnt classifier is trained based on the uncertainty level given the scan configuration, scan settings, reconstruction of the cardiac data, patient characteristics, and/or other factors. The latin hypercube sampling method or any other sampling method (e.g., Monte Carlo method, Polynomial Chaos Expansion, Stochastic Collocation, etc.) defines a set of n samples for the uncertain variable (e.g., radii). A uniform distribution between 0 and 1 is considered, and the resulting values are then mapped to an uncertainty interval for the radius (e.g., −0.2 mm; 0.2 mm). Various other types of uncertain distributions may be used, like normal, log-normal, etc., based on the available prior information (i.e., uncertainties of the contributing factors). The uncertainty distributions may be used to define absolute or relative variations in radius. The uncertainty a represents a distribution of noise to be added to the variable, such as the radius.

For each location, the radius value is initialized by summing up the baseline radius value with the value of the uncertain variable, as represented by: $r_i^j = r^j + \alpha_i^j$, where j refers to the location (sampling of the distribution of the random variable), and i refers to the current sample (e.g., the radius at a given location).

For all cross-sections not part of the subset, the corresponding radius variation is computed by interpolating between the random values of the two neighboring cross-sections of the subset. This variation is summed up with the baseline radius value of the location. Radius values are provided for each location.

FFR is computed at all locations of interest defined a priori by applying the predictor for the geometry sample generated at the previous step→$FFR_i(x_k)$. For each spatial location of interest k, tens, hundreds, or thousands of FFR quantifications are performed. For each sample i of the distribution, an FFR quantification is performed. Where a machine-learnt predictor quantifies, the sampling may be performed more rapidly than using CFD.

The standard deviation of the FFR values at each location, k, of interest is computed, as represented by:

$$\sigma_k = \sqrt{\frac{1}{n-1} \sum_i (FFR_i(x_k) - \overline{FFR(x_k)})^2}.$$

The standard deviation for each location or a subset of locations is computed.

The correlations between the uncertain variables and the FFR values at the locations of interest $x_k$ are computed, as represented by:

$$\rho_k^j = \mathrm{corr}(\alpha^j, FFR(x_k)).$$

The distribution of the uncertainty and the distribution of FFR values for the location based on the sampling are correlated.

The sensitivities associated with each uncertain variable is computed as the absolute value of the product between the correlations and the FFR standard deviations at the locations of interest. This computation is represented by:

$$s_k^j = |\rho_k^j \sigma_k|$$

The correlation values enable a ranking of the uncertain variables with respect to the output measure (i.e., which uncertain variables are most and least responsible for the FFR variation are determined). By multiplying the correlation values with the standard deviation, the former is scaled and a score is obtained that evaluates how much an uncertain variable is responsible for a quantitative variation of FFR. For example, if the correlation of an uncertain variable is high but the standard deviation is low, the sensitivity value will be relatively low.

The result is a sensitivity map showing sensitivity of a quantification at one location to uncertainty at other locations. A sensitivity map is computed separately for each quantification location of interest. For example, the sensitivity value at each location of the subset is set equal to the sensitivity of the uncertain variable associated to that cross-section segment. The sensitivities at the remaining cross-sections are set by interpolating between the values of the neighboring cross-sections.

In the second embodiment, the sensitivity of the value and other values at other locations to the uncertainty at a given location is determined. For example, sensitivities are computed with respect to a certain lesion. The sensitivities of the quantities of interest at all or other locations of an anatomical model are determined with respect to the uncertainty of the reconstruction of a certain lesion. In the example below, the sensitivity to FFR quantification is used.

A lesion of interest (e.g., stenosis) is chosen automatically or by the operator. For example, the most significant stenosis in the entire anatomical model may be selected.

The uncertain input variables $\alpha^j$ are defined, such as discussed above. A subset of all locations (cross-sections) of the lesion is selected based on a given spacing (e.g. 0.1 mm), and one uncertain variable is associated with each selected location. Alternatively, separate uncertain variables may be associated to the top, minimum, and/or bottom radius of the lesion.

The latin hypercube sampling method or any other available sampling method defines a set of n samples for the uncertain variables. A uniform distribution between 0 and 1 is considered, and the resulting values are then mapped to an uncertainty interval for the radius (e.g., −0.2 mm; 0.2 mm). Various other types of uncertain distributions may be used, such as normal, log-normal, etc. based on the available prior information.

For each location of the subset, the radius value is initialized by summing up the baseline radius value with the value of the uncertain variable: $r_i^j = r^j + \alpha_i^j$. For all cross-sections of the lesion that were not selected in the subset, the corresponding radius variation is computed by interpolating between the random values of the two neighboring cross-sections that were selected in the subset. This interpolated α value is summed up with the baseline radius value of the location.

FFR is computed at all locations of the anatomical model for the geometry sample generated at the previous step→$FFR_i(x)$. The standard deviation of the FFR values at all locations of the anatomical model is computed as:

$$\sigma(x) = \sqrt{\frac{1}{n-1} \sum_i (FFR_i(x) - \overline{FFR(x)})^2}$$

The correlations between the uncertain variables and the FFR values at all locations of the anatomical model are computed as:

$$\rho^j(x) = \mathrm{corr}(\alpha^j, FFR(x))$$

The sensitivities associated with each uncertain variable, computed as the absolute value of the product between the correlations and the FFR standard deviations at all locations of the anatomical model, are determined as $$s^j(x) = |\rho^j(x) \sigma(x)|.$$

Based on these sensitivities, the most significant locations of the lesion of interest in terms of uncertainty (i.e., the uncertainty of which locations has the largest effect on the computed measure of interest) may be determined. This determination is provided for any location spaced from the lesion as well as for locations in the lesion.

The process may be repeated for other lesions. Sensitivity maps for the different lesions are provided separately. Alternatively, the sensitivities from different lesions may be combined (e.g., maximum or average), indicating locations of FFR most effected by uncertainty from multiple lesions.

For either the first or second embodiment, based on the selection of a lesion or location of interest and the definition of uncertain variables for that lesion or location, various statistical information for the measure of interest may be determined at the location and other locations of the anatomical model. Other statistical information may include probability distribution function, mean+/−standard deviation, mean and the 90%/95%/99% confidence intervals, skewness, kurtosis, cumulative distribution/belief/plausibility functions as a continuous function or for various response levels, simple/partial/simple rank correlation matrix between each uncertain input variable and the measure of interest, and/or global sensitivity indices (e.g., main effects and total effects for the measure of interest).

Other calculations of sensitivity, uncertainty, or another statistical parameter may be used in either embodiment. The spatial relationship between the geometry and quantification is provided as a sensitivity map. The map indicates what geometry may contribute what level of uncertainty to sensitivity of the quantification and/or at what locations sensitivities of the quantifications are affected by geometry at another location.

In act 28, the image processor generates an output based on the value of the hemodynamic quantification and the value or values of the uncertainty and/or sensitivity. The output is transmitted to a display, such as a monitor, workstation, printer, handheld, or computer. The output may be provided on a display of the medical imaging system. Alternatively or additionally, the transmission is to a memory, such as a database of patient records, or to a network, such as a computer network.

The output provides diagnostic or prognostic information for the physician. The physician may make a clinical decision or recommendation based on the output. For example, a radiologist may use the output to determine what measure or treatment to perform or how much time to spend on any measure or treatment.

In one embodiment, the output is alphanumeric text of the value of the hemodynamic quantification and the value or values of the uncertainty and/or sensitivity. For example, an image of the patient-specific geometry or rendered from the cardiac data includes an annotation or overlay indicating the FFR and sensitivity or uncertainty level for a given location. Any point on the image may be queried (point and click) for the associated value of the measure of interest and its sensitivity, uncertainty and/or confidence intervals, and the corresponding values are shown overlaid to the image. As an example, the FFR and sensitivity values are shown in an image at or near points of interest in the coronary arteries. Alternatively, the user can activate a "no click" mode, in which case the measure of interest and its sensitivity, uncertainty, and/or confidence intervals are displayed in correspondence of the cursor by just positioning the cursor on the position of interest. Given the spatial distribution of sensitivity and/or uncertainty, the level of effect of the geometry at each location relative to a quantification or the sensitivity of a quantification at one location to uncertainty at another location may be indicated. As the user selects or moves the cursor, the corresponding information is provided. In another approach, the sensitivity of a selected location to uncertainty at another selected location is shown.

Figure 7:
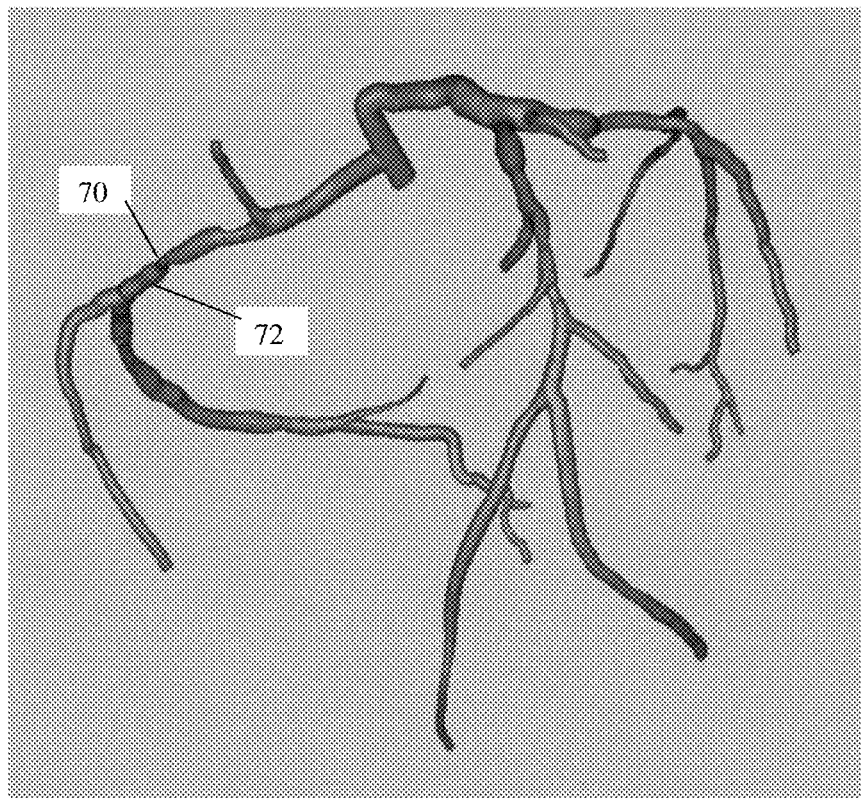
FIG. 7 shows an example display of a map of sensitivity by location along a vessel tree.

The output may be an image. For example, the anatomical model of the coronary artery is color coded based on the values of the measure of interest and/or any corresponding sensitivity, uncertainty, and/or confidence intervals (one or more continuous or discrete color maps may be used for this purpose). FIG. 7 illustrates an example of a discrete sensitivity color map (shown in grayscale) for an anatomical model reconstructed from coronary computed tomography angiography (CCTA) data. Lighter gray (red) corresponds to low sensitivity, medium gray (green) to medium sensitivity and dark gray (blue) to high sensitivity. The sensitivities are for geometric locations relative to one FFR value, such as an FFR value from location 72 just beyond a stenosis 70. While FIG. 7 is a three-dimensional rendering from the determined patient-specific geometry, a two-dimensional cross section or flattened 2D map (e.g., projection) of the 3D vessel geometry may be used.

The measures of interest may interactively reflect changes in the feature set. If the user chooses to alter the value of any feature or the geometry, the value of the measure of interest and its sensitivity, uncertainty, and/or confidence intervals are updated to reflect the response to the alteration.

Where different modalities or different acquisitions from the same modality (one for feature extraction, another one for visualization) are used, registration of the images and features (spatial and temporal) is performed. The systems may be calibrated to account for different coordinate systems, landmarks may be registered, or the user may manually align images. Where the same scanner is used during examination and visualization, features may include table position, angulations, etc.

Where the sensitivity of a quantification at one location to uncertainties at other locations is determined, separate sensitivity maps may be generated for each location of interest (i.e., each location for which sensitivity and quantification are performed). The resulting sensitivity maps may be shown separately or combined. To combine, a mathematical operator (e.g. maximum, minimum, or average) combines the sensitivity for each location from the different maps.

Where the sensitivity for quantification spaced from a location as the source of uncertainty is used, the sensitivity map reflects the level of contribution to the sensitivity due to the uncertainty at that source. Both types of maps of spatial distribution of uncertainty and/or sensitivity may be displayed.

In act 30 of FIG. 1, the image processor compares the sensitivity and/or uncertainty to a threshold. The comparison may be part of any sequence or rule system. The comparison is to identify quantification for which sufficient confidence is provided from quantification with insufficient confidence. A recommendation may be output based on the comparison, such as to verify or improve accuracy of geometric fit and where.

In one embodiment, the comparison is part of a decision support system based on interactive sensitivity analysis. The uncertainty associated with the measure of interest may play a role in the clinical workflow. This is particularly true when the measure of interest (e.g. FFR) is used as part of a decision-making process, such as when the treatment of choice for the patient depends on the value of the measure of interest (e.g. PCI for FFR<0.8, optimal medical therapy otherwise). In this context, it is important to know if the uncertainty associated with the measure of interest is such that a clear decision cannot be confidently made, such as where computed FFR is 0.82 but its standard deviation is larger than 0.02.

The decision support system is based on the evaluation of uncertainty of the measure of interest. In an example approach, FFR is used as a criterion for deciding the treatment of the patient, either based on a direct decision strategy (PCI for computed FFR below a certain threshold) or a hybrid decision strategy. If uncertainty is too high, further processing may be recommended to reduce uncertainty. A course of action based on predicted FFR and its uncertainty is recommended.

Evaluating whether or not uncertainty is too high depends on the criterion used in the clinical decision-making process. If computed FFR is used as main determinant for the choice of the course of action, and the decision is based on FFR being above or below a given threshold τ (e.g. ρ=0.8), then uncertainty may be defined as too high in case the estimated standard deviation of FFR is such that $$FFR(x_k) < \tau \text{ and } FFR(x_k) + \sigma_k(x_k) > \tau, \text{ or}$$

$$FFR(x_k) > \tau \text{ and } FFR(x_k) - \sigma_k(x_k) < \tau$$

In a hybrid decision strategy, generally two metrics are concurrently used to assess functional severity of the considered lesion. A combination of computed FFR and invasively measured FFR is used. Two thresholds $\tau_h$ and $\tau_l$ are identified, such that $0 \leq \tau_l \leq 0.8 \leq \tau_h \leq 1$, and the decision strategy is: stenosis not functionally significant if computed FFR>$\tau_h$, stenosis functionally significant if computed FFR<$\tau_l$. If $\tau_l$ computed FFR≤$\tau_h$ ("grey zone"), then stenosis severity is assessed based on invasively measured FFR. In this context, uncertainty of computed FFR may be defined as too high if by correcting FFR by the estimated standard deviation, the resulting value crosses a threshold (either $\tau_l$ or $\tau_h$).

Alternatively, uncertainty itself may be used as a decision criterion. If the estimated standard deviation is larger than a given threshold $\tau_{std}$, the computed FFR value is assigned to the grey zone by default. One possible approach to defining $\tau_{std}$ is as follows. Consider a database of synthetically generated geometries. For all the geometries in the database, the likelihood of reclassification due to uncertainty is computed. One possible way to implement this is considering confidence intervals for computed FFR at the locations of interest, under the assumption of normal distribution. A lesion is defined as "likely to be reclassified" if there exist FFR values within the 95% confidence interval at the location of interest for which the lesion characterization would change. As an example, in a direct decision strategy with a single location of interest downstream of a stenosis, the stenosis is likely to be reclassified if computed FFR is 0.82 and standard deviation is x such that 0.82−1.96x<0.8, or x>0.01. The optimal threshold $\tau_{std}$ for the standard deviation is then expressed as a function of the percentage of cases likely to be reclassified in the considered database (e.g., the value of $\tau_{std}$ is defined as the standard deviation for computed FFR that causes 10% or more of the stenoses in the database to be likely reclassified). Different thresholds $\tau^k_{std}$ may be defined for different classes of geometries (e.g. different vessels, different kinds of stenoses, in general different geometry features) by properly populating the considered database of synthetically generated geometries. For instance, different thresholds may be defined for the left vs the right coronary tree, by considering different databases representing geometry features typical of the left or the right tree respectively.

Because of performing the uncertainty and/or sensitivity analysis (e.g. uncertainty is too high), the reconstructed anatomical model may be modified automatically and/or manually. Following the modification of the anatomical model, the uncertainty in those regions may also be reduced, resulting in smaller uncertainty and/or sensitivity values for the quantities of interest. The result may be a change in recommendation or a more definitive outcome. The system may also recommend invasive measurement of FFR as a substitute for computed FFR, for instance, in the case in which uncertainty levels force computed FFR in the grey zone in a hybrid decision strategy despite any change in accuracy of geometric fit. Alternatively, no modification is needed or possible.

In act 32, the image processor receives a modification of the patient-specific cardiac geometry and/or other feature. The received modification is the result of manual or automatic change. For example, the modification is received from user input, such as the user adjusting a fit of the geometry for the patient. Following a closer inspection at highly sensitive locations (e.g., stenosis locations), the user changes the geometric fit to better match the patient at those locations. Alternatively, the image processor applies further fitting or more refined processing to improve the accuracy of the fit at locations contributing the most to uncertainty. For example, the value of one or more parameters used for fitting the anatomical model to the patient is altered to attempt a different fit. Alternatively, the medical images may be reacquired, with different scan properties, and a completely new anatomical model may be generated. Furthermore, alternative definitions of the local anatomy may be generated with different models or approaches.

Once the modification is received, the predication of the quantification and the classification of the uncertainty and/or sensitivity are repeated. The values of features are extracted again from the modified geometry and used to redo the analysis.

FIGS. 8-19 show example results. Example sensitivity values are computed for three patients using the embodiment where the uncertainties at other locations contributing to the sensitivity of quantification at a location of interest (e.g., beyond a stenosis) are determined. The anatomical models have been reconstructed from X-ray angiographic data, the measure of interest is FFR, and the sensitivity is with respect to the radii of the geometry.

Figure 8:
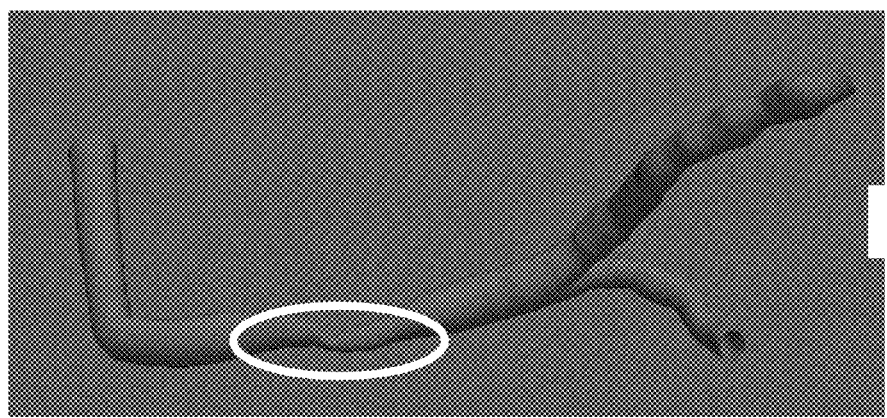
FIGS. 8, 11, and 14 show example geometric models for three different patients.
Figure 9:
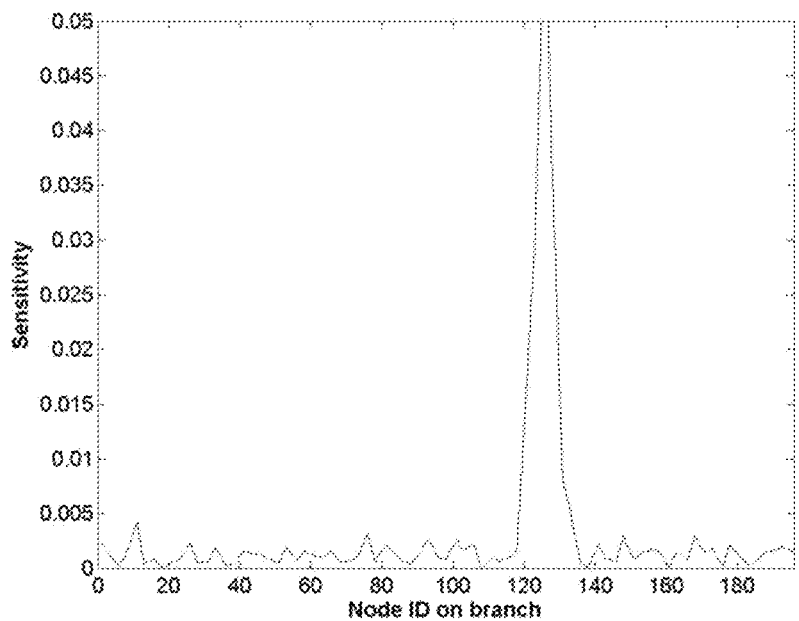
FIGS. 9, 12 and 15 show graphs of sensitivity as a function of location along main branches of the models of FIGS. 8, 11, and 14, respectively.
Figure 10:
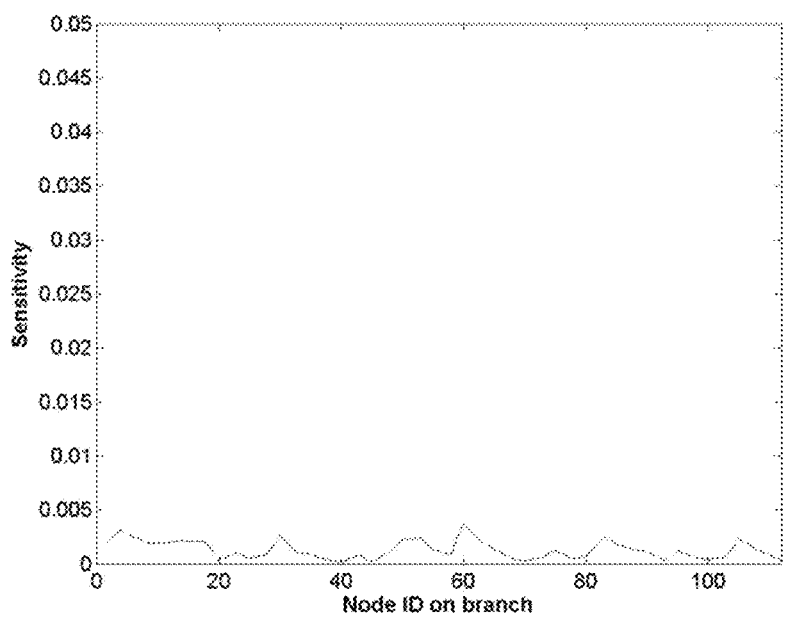
FIGS. 10, 13, and 16 show graphs of sensitivity as a function of location along daughter branches of the models of FIGS. 8, 11, and 14, respectively.

FIG. 8 shows the anatomical model of the first patient. The main stenosis is on the parent branch, as indicated by the oval. FIGS. 9 and 10 show the sensitivities along the centerlines of the parent branch and the main daughter branch, respectively. The highest sensitivity is obtained for the locations in the minimum radius region of the main stenosis on the parent branch.

Figure 11:
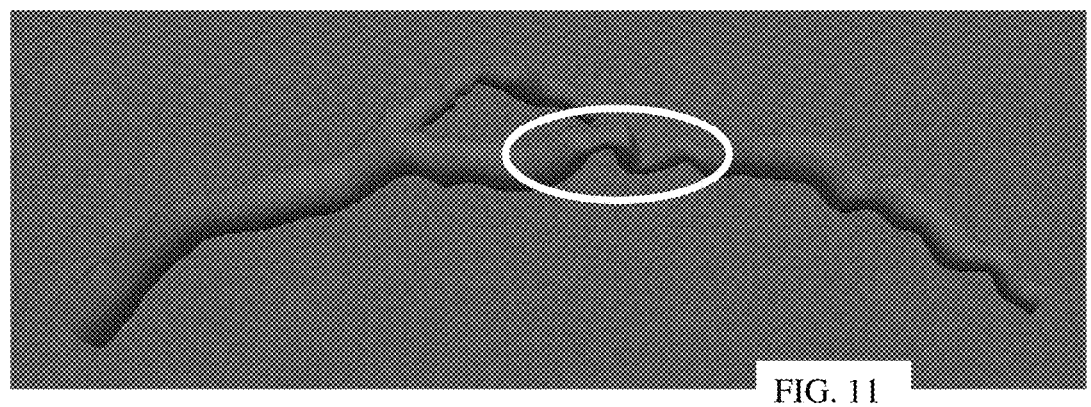
Figure 12:
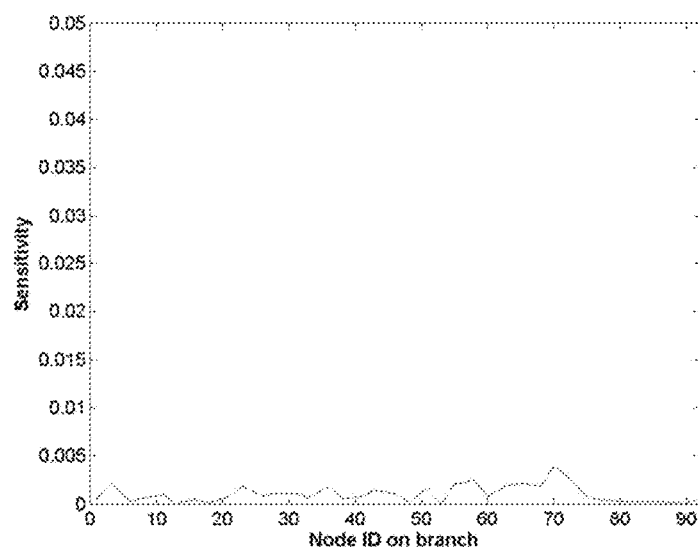
Figure 13:
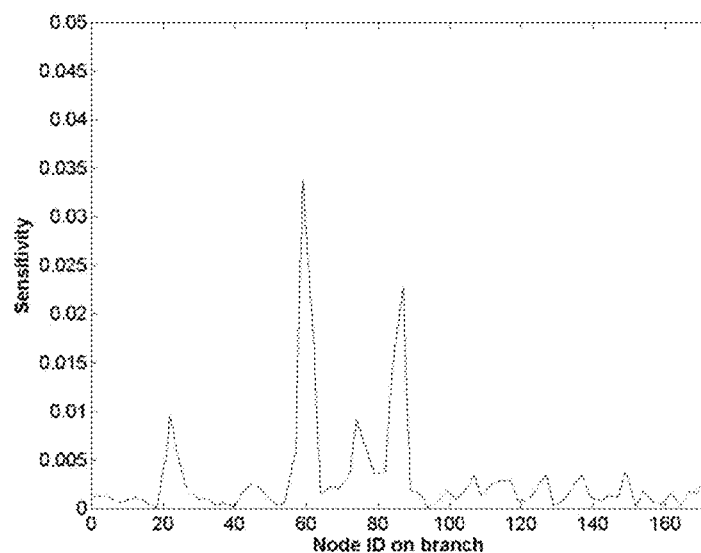

FIG. 11 shows the anatomical model of the second patient. The main stenosis is on the main daughter branch, as indicated by the oval. FIGS. 12 and 13 show the sensitivities along the centerlines of the parent branch and the main daughter branch, respectively. The highest sensitivity is obtained for the locations in the minimum radius region of the main stenosis on the main daughter branch. The two largest spikes correspond to two locations which have similar (minimum) radius values.

Figure 14:
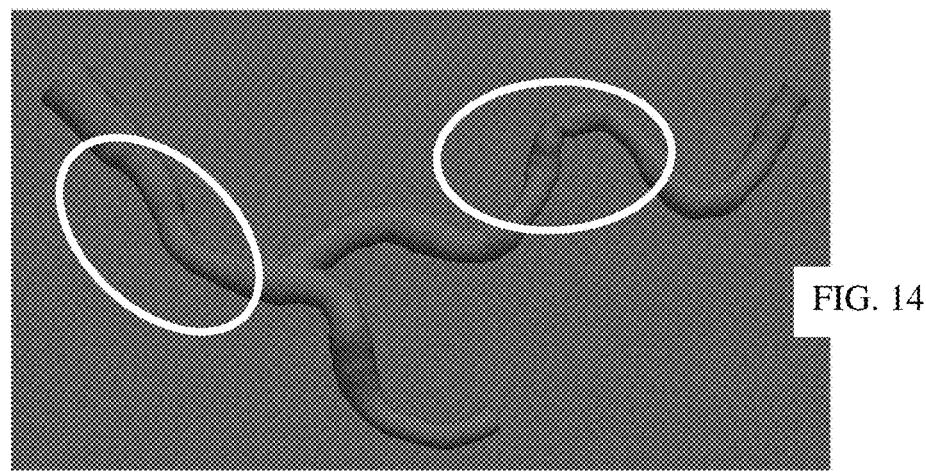
Figure 15:
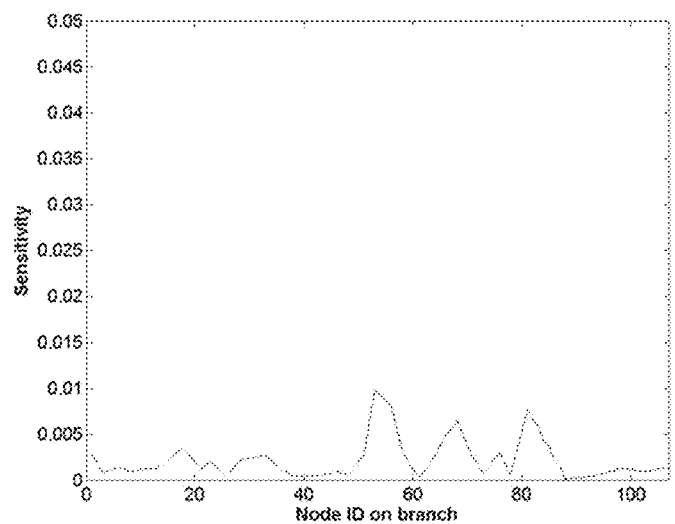
Figure 16:
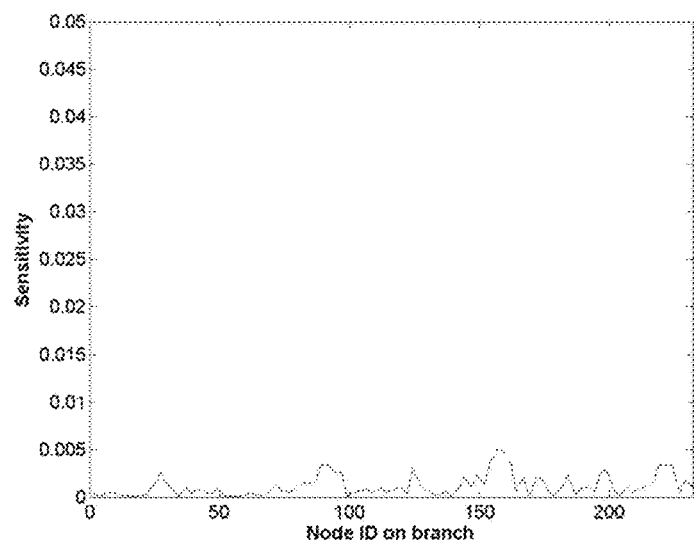

FIG. 14 shows the anatomical model of the third patient. The main stenosis is on the parent branch, as indicated by the oval. There is also a mild stenosis on the daughter branch, as indicated by another oval. FIGS. 15 and 16 show the sensitivities along the centerlines of the parent branch and the main daughter branch, respectively. The highest sensitivity is obtained for the locations in the minimum radius region of the main stenosis on the parent branch. The sensitivity around the mild stenosis of the main daughter branch is much smaller.

In any of these examples, the user or the image processor may modify the fit for the locations of the highest sensitivity. As a result, the confidence in the quantification may be increased.

Figure 17:
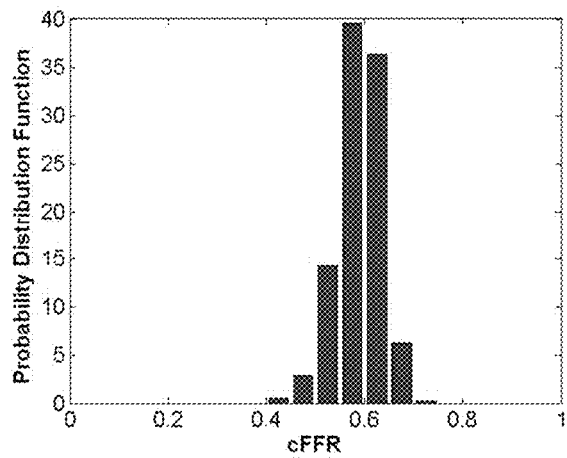
FIGS. 17-19 show probability distribution functions of the hemodynamic quantity for each of LAD, LCx, and RCA locations, respectively, of the coronary geometry of the vessel tree of FIG. 7.
Figure 18:
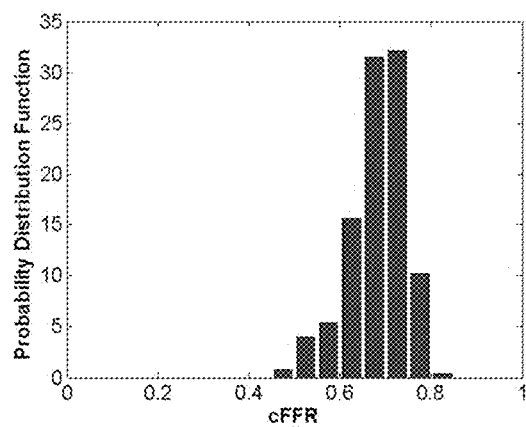
Figure 19:
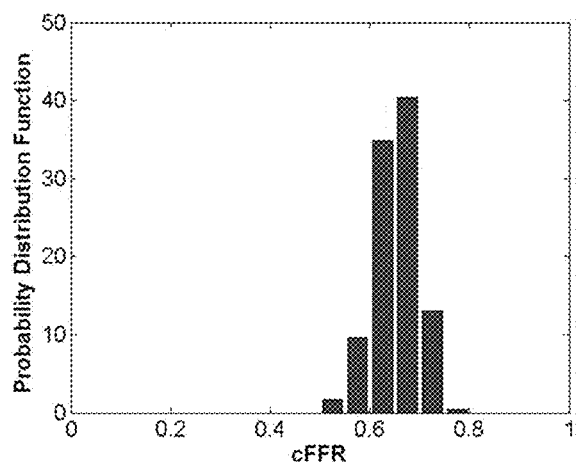

FIGS. 17-19 show probability distributions for the FFR values computed at distal locations on the LAD, LCx and RCA respectively for the anatomical model in FIG. 7. Given the uncertainty, the probability distributions show the likely FFR values.

FIG. 20 shows a system for hemodynamic quantification, such as a system for FFR quantification with spatial relationship of sensitivity and/or uncertainty. The system implements the method of FIG. 1, method of FIG. 2, or another method to output quantification and corresponding statistical information.

The system includes a medical scanner 80, an image processor 82, a memory 84, a graphical user interface (GUI) 88 with a user input 85 and a display 86, and one or more machine-learnt predictors or classifiers 90. Additional, different, or fewer components may be provided. For example, a network or network connection is provided, such as for networking with a medical imaging network or data archival system or networking between the medical scanner 80 and the image processor 82. In another example, the user input 85 is not provided. As another example, a server is provided for implementing the image processor 82 and/or machine-learnt classifiers 90 remotely from the medical scanner 80.

The image processor 82, memory 84, user input 85, display 86, and/or machine learnt classifiers 90 are part of the medical scanner 80. Alternatively, the image processor 82, memory 84, user input 85, display 86, and/or machine learnt classifiers 90 are part of an archival and/or image processing system, such as associated with a medical records database workstation or server, separate from the medical scanner 80. In other embodiments, the image processor 82, memory 84, user input 85, display 86, and/or machine learnt classifiers 90 are a personal computer, such as desktop or laptop, a workstation, a server, a network, or combinations thereof.

The medical scanner 80 is a medical diagnostic imaging CT system. A gantry supports a source of x-rays and a detector on opposite sides of a patient examination space. The gantry moves the source and detector about the patient to perform a coronary CT angiography scan. Various x-ray projections are acquired by the detector from different positions relative to the patient. Computed tomography solves for the two or three-dimensional distribution of the response from the projections. In other embodiments, the medical scanner 80 is an ultrasound, x-ray, fluoroscopy, positron emission tomography, single photon emission computed tomography, or magnetic resonance system.

The memory 84 may be a graphics processing memory, a video random access memory, a random-access memory, system memory, cache memory, hard drive, optical media, magnetic media, flash drive, buffer, database, combinations thereof, or other now known or later developed memory device for storing data. The memory 84 is part of the medical scanner 80, part of a computer associated with the image processor 82, part of a database, part of another system, a picture archival memory, or a standalone device.

The memory 84 stores patient data, such as in a computerized patient record. Any of the patient data discussed herein may be stored, such as coronary CT data, fit models, parameters from fit models, measurements, clinical data, non-invasive test results, and/or biochemical measurements. The memory 84 alternatively or additionally stores a matrix or matrices embodying one or more machine-learnt predictors or classifier 90. Rule-based or other predictors may be stored. The memory 84 may alternatively or additionally store data during processing, such as storing information discussed herein or links thereto.

The memory 84 or other memory is alternatively or additionally a non-transitory computer readable storage medium storing data representing instructions executable by the programmed image processor 82 or a processor implementing the hemodynamic quantification with statistical information. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 82 is a general processor, central processing unit, control processor, graphics processor, digital signal processor, three-dimensional rendering processor, application specific integrated circuit, field programmable gate array, digital circuit, analog circuit, combinations thereof, or other now known or later developed device for quantification prediction with classification of uncertainty and/or sensitivity as a function of location. The image processor 82 is a single device or multiple devices operating in serial, parallel, or separately. The image processor 82 may be a main processor of a computer, such as a laptop or desktop computer, or may be a processor for handling some tasks in a larger system, such as in the CT scanner 80. The image processor 82 is configured by instructions, design, hardware, and/or software to perform the acts discussed herein.

The image processor 82 is configured to extract a patient-specific geometry from coronary data. Similarly, the image processor 82 acquires and/or extracts an input feature vectors from the coronary data, the geometry, and/or the computerized patient record. The image processor 82 is configured to apply the input feature vector to a predicator of quantification, such as a machine-learnt predictor 90 or a CFD model. The predictor computes a hemodynamic quantity for one or more locations on the patient-specific coronary geometry.

The image processor 82 is configured to determine uncertainty, sensitivity, and/or standard deviation of the hemodynamic quantity associated with different locations. The statistical information is determined using a machine-learnt classifier 90 or by statistical sampling. The image processor 82 determines the uncertainty, sensitivity, and/or standard deviation at each of the location of the quantification and other locations along the geometry centerline. In one embodiment, the uncertainty, sensitivity, and/or standard deviation is determined as a contribution from the various locations to the hemodynamic quantity of a given location. In another embodiment, the uncertainties, sensitivities, and/or standard deviations of the hemodynamic quantities at various locations are determined based on variation or uncertainty of a given location.

The machine-learnt predicators and/or classifiers 90 are implemented by the image processor 82 or other processor with access to the matrices defining the predictors and/or classifiers 90 stored in the memory 84 or other memory. The machine-learnt predictors and/or classifiers 90 are matrices of inputs (i.e., values of features in the input vector), weights, relationships between weighted inputs or other layers, and outputs.

The image processor 82 may be configured to generate a graphic user interface (GUI) 88 for input of values or data and/or for outputting information. The GUI 88 includes one or both of the user input 85 and the display 86. The GUI 88 provides for user interaction with the image processor 82, medical scanner 80, and/or machine-learnt predictors and/or classifiers 90. The interaction is for inputting information (e.g., selecting patient files) and/or for reviewing output information (e.g., viewing patient-specific geometry and sensitivity maps). The GUI 88 is configured (e.g., by loading an image into a display plane memory) to display the outputs.

The user input device 85 is a keyboard, mouse, trackball, touch pad, buttons, sliders, combinations thereof, or other input device. The user input 85 may be a touch screen of the display 86. User interaction is received by the user input device 85, such as a designation of a location. Other user interaction may be received, such as for activating the classification.

The display 86 is a monitor, LCD, projector, plasma display, CRT, printer, or other now known or later developed devise for outputting visual information. The display 86 receives images of graphics, text, quantities, spatial distribution of anatomy or function, or other information from the image processor 82, memory 84, CT scanner 80, or machine-learnt classifiers 90.

One or more images are displayed. The images may or may not include anatomical representation or imaging, such as an anatomical image from the coronary CT data or a rendering of the patient-specific geometry. The image includes a hemodynamic quantity and confidence statistical information (e.g., uncertainty, sensitivity, standard deviation, and/or confidence intervals). The image includes an indication, such as a text, a graphic, or colorization, of the predication and/or classification of the patient for the decision. In one embodiment, a map of the statistical information is output as an image, such as color modulation for sensitivity or uncertainty as a function of location on an image of geometry or a rendering form coronary data.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for hemodynamic quantification in a medical imaging system, the method comprising:
scanning a patient with the medical imaging system, the scanning providing cardiac data representing part of a cardiac system of the patient;
determining a patient-specific cardiac geometry from the cardiac data;
extracting values for features of a first input vector of a machine-learnt predictor of the hemodynamic quantification from the patient-specific cardiac geometry;
predicting, by the machine-learnt predictor, a value of the hemodynamic quantification in response to the values of the features of the first input vector;
extracting values for features of a second input vector of a machine-learnt classifier of uncertainty and/or sensitivity of the hemodynamic quantification;
classifying, by the machine-learnt classifier, a contribution to a value or values of the uncertainty and/or sensitivity of the hemodynamic quantification from locations in the patient-specific cardiac geometry in response to the values for the features of the second input vector; and
generating an output based on the value of the hemodynamic quantification and the value or values of the uncertainty and/or sensitivity.

2. The method of claim 1 wherein determining the patient-specific geometry comprises fitting a model to the cardiac data.

3. The method of claim 1 wherein extracting the values for the features of the first input vector and/or the second input vector comprises extracting radii along a vessel represented by the patient-specific cardiac geometry.

4. The method of claim 1 wherein predicting comprises predicting with the machine-learnt predictor trained, at least in part, on synthetic samples.

5. The method of claim 1 wherein predicting comprises predicting a fractional flow reserve as the hemodynamic quantification.

6. The method of claim 1 wherein classifying comprises classifying with the machine-learnt classifier trained based on an uncertainty level based on a scan configuration, reconstruction of the cardiac data, and/or patient characteristics.

7. The method of claim 1 wherein classifying comprises classifying with the machine-learnt classifier trained based on a distribution of the hemodynamic quantification given a sampled distribution of noise.

8. The method of claim 1 wherein classifying comprises classifying with the machine-learnt classifier trained based on sensitivities from a standard deviation of the distribution of the hemodynamic quantification and a correlation of an uncertain variable with a distribution of the hemodynamic quantification.

9. The method of claim 1 wherein predicting comprises predicting the value of the hemodynamic quantification for a first location,
wherein classifying comprises classifying for each of a plurality of second locations, and
wherein generating the output comprises generating a map of the second locations showing contribution to uncertainty and/or sensitivity to the value of the hemodynamic quantification at the first location.

10. The method of claim 1 wherein predicting comprises predicting the value and other values of the hemodynamic quantification for a plurality of first locations, and
wherein classifying comprise classifying the sensitivity of the value and other values to the uncertainty at a second location.

11. The method of claim 1 further comprising separating the patient-specific cardiac geometry into vessel branches and performing the predicting and classifying separately for each of the vessel branches.

12. The method of claim 1 wherein generating comprises generating a map of the sensitivity and/or uncertainty of the hemodynamic quantification as a function of location of the patient-specific cardiac geometry.

13. The method of claim 1 wherein generating comprises generating an output as alphanumeric text of the value of the hemodynamic quantification and the value or values of the uncertainty and/or sensitivity.

14. The method of claim 1 further comprising receiving user selection of a location of the patient-specific cardiac geometry and wherein generating comprises generating the output as the value of the hemodynamic quantification for the location and at least the value or values of the uncertainty and/or sensitivity.

15. The method of claim 1 further comprising receiving a modification of the patient-specific cardiac geometry and repeating the predicting and classifying based on the patient-specific cardiac geometry with the modification.

16. The method of claim 1 further comprising comparing the value of the uncertainty to a threshold, and outputting a recommendation based on a result of the comparison.

17. A system for hemodynamic quantification, the system comprising:
a medical scanner for scanning a patient, the medical scanner configured to output coronary data for the patient;
an image processor configured to extract a patient-specific coronary geometry from the coronary data, compute a hemodynamic quantity for a first location on the patient-specific coronary geometry, determine a confidence statistic of the hemodynamic quantity, the confidence statistic indicating a contribution to the hemodynamic quantity from a second location on the patient-specific coronary geometry different than the first location; and
a display configured to display the hemodynamic quantity and the confidence statistic.

18. The system of claim 17 wherein the image processor is configured to determine the confidence statistic at each of the second location, the first location, and a plurality of third locations of the patient-specific cardiac geometry, and
wherein the display is configured to display a map of the determined confidence statistics.

19. The system of claim 17 wherein the image processor is configured to determine the confidence statistic as uncertainty, sensitivity, and/or standard deviation of the hemodynamic quantity by application of a machine-learnt classifier.

20. The system of claim 17 wherein the image processor is configured to compute the hemodynamic quantity for each of the first location and the second location, and
wherein the image processor is configured to determine the confidence statistics of the hemodynamic quantities based on variation of the second location.

* * * * *